US011284842B2

(12) United States Patent
Dirkes et al.

(10) Patent No.: US 11,284,842 B2
(45) Date of Patent: Mar. 29, 2022

(54) METHOD OF ASSESSING THE RELIABILITY OF A BLOOD PRESSURE MEASUREMENT AND AN APPARATUS FOR IMPLEMENTING THE SAME

(71) Applicant: KONINKLIJKE PHILIPS N.V., Eindhoven (NL)

(72) Inventors: Marcel Cornelis Dirkes, The Hague (NL); Charles Frederik Sio, Eindhoven (NL); Murtaza Bulut, Eindhoven (NL); Maarten Petrus Joseph Kuenen, Noord Brabant (NL)

(73) Assignee: Koninklijke Philips N.V., Eindhoven (NL)

( * ) Notice: Subject to any disclaimer, the term of this patent is extended or adjusted under 35 U.S.C. 154(b) by 917 days.

(21) Appl. No.: 16/065,259

(22) PCT Filed: Dec. 22, 2016

(86) PCT No.: PCT/EP2016/082367
§ 371 (c)(1),
(2) Date: Jun. 22, 2018

(87) PCT Pub. No.: WO2017/109064
PCT Pub. Date: Jun. 29, 2017

(65) Prior Publication Data
US 2021/0169425 A1    Jun. 10, 2021

(30) Foreign Application Priority Data
Dec. 22, 2016  (EP) ..................... 15202305

(51) Int. Cl.
*A61B 5/02*    (2006.01)
*A61B 5/00*    (2006.01)
(Continued)

(52) U.S. Cl.
CPC .......... *A61B 5/7221* (2013.01); *A61B 5/0205* (2013.01); *A61B 5/0531* (2013.01);
(Continued)

(58) Field of Classification Search
CPC ....... A61B 5/7221; A61B 5/0531; A61B 5/28; A61B 5/0205; A61B 5/4824; A61B 5/165;
(Continued)

(56) References Cited

U.S. PATENT DOCUMENTS 9,936,920 B2    4/2018  Muehlsteff
2004/0147848 A1  7/2004  Shirasaki et al.
(Continued)

FOREIGN PATENT DOCUMENTS

CN    204839492    12/2015
GB    2516220 A    1/2015
(Continued)

OTHER PUBLICATIONS

Abir-Khalil et al., "Prevalence of and Predictors of White-Coat Hypertension in a Large Database of Ambulatory Blood Pressure Monitoring", East Mediterr. Health Journal, 15 (2): 400-7, Mar-Apr. 2009, PMID19554987.
(Continued)

*Primary Examiner* — Amanda K Hulbert
*Assistant Examiner* — Natasha Patel (57) ABSTRACT

There is provided a method of assessing the reliability of a measurement of blood pressure of a subject, the method in a control unit of an apparatus comprising obtaining a first measurement of at least one physiological characteristic of the subject that is indicative of the level of pain and/or stress of the subject, wherein the first measurement is made prior to a measurement of blood pressure being made; obtaining the measurement of blood pressure of the subject; obtaining
(Continued)

a second measurement of the at least one physiological characteristic of the subject, wherein the second measurement is made after the measurement of blood pressure is made and prior to a subsequent measurement of blood pressure being made; and determining if the measurement of blood pressure is reliable based on the first measurement and the second measurement, wherein the measurement of blood pressure is determined to be reliable if the first measurement and the second measurement indicate a low level of pain and/or stress. A corresponding apparatus that implements the method is also provided.

15 Claims, 4 Drawing Sheets

(51) Int. Cl.
| | |
|---|---|
| *G16H 50/20* | (2018.01) |
| *G16H 40/40* | (2018.01) |
| *G16H 40/60* | (2018.01) |
| *G16H 40/63* | (2018.01) |
| *A61B 5/28* | (2021.01) |
| *A61B 5/0205* | (2006.01) |
| *A61B 5/0531* | (2021.01) |
| *A61B 5/16* | (2006.01) |
| *A61B 5/022* | (2006.01) |
| *A61B 5/024* | (2006.01) |

(52) U.S. Cl.
CPC ............... *A61B 5/165* (2013.01); *A61B 5/28* (2021.01); *A61B 5/4824* (2013.01); *G16H 40/40* (2018.01); *G16H 40/60* (2018.01); *G16H 40/63* (2018.01); *G16H 50/20* (2018.01); *A61B 5/022* (2013.01); *A61B 5/02405* (2013.01); *A61B 2562/0247* (2013.01)

(58) Field of Classification Search
CPC ............ A61B 5/022; A61B 2562/0247; A61B 5/02405
See application file for complete search history.

(56) References Cited

U.S. PATENT DOCUMENTS

| | | | |
|---|---|---|---|
| 2006/0058590 A1* | 3/2006 | Shaw | A61B 5/412 600/301 |
| 2008/0287814 A1* | 11/2008 | Muehsteff | A61B 5/721 600/490 |
| 2009/0156946 A1 | 6/2009 | Lane | |
| 2010/0249556 A1 | 9/2010 | Sethi | |
| 2010/0305459 A1 | 12/2010 | Whitt et al. | |
| 2013/0158417 A1* | 6/2013 | Borger | A61B 5/0225 600/485 |
| 2015/0057554 A1 | 2/2015 | Watson | |
| 2016/0100787 A1* | 4/2016 | Leung | A61B 5/0082 600/480 |

FOREIGN PATENT DOCUMENTS

| | | |
|---|---|---|
| WO | WO2005020808 A1 | 3/2005 |
| WO | WO2012027613 A1 | 3/2012 |

OTHER PUBLICATIONS

Handler, J., "The Importance of Accurate Blood Pressure Measurement", The Permanente Journal, vol. 13, No. 3, 2009, pp. 51-54.
"Blood Pressure Measurement Toolkit: Improving Accuracy, Enhancing Care", Wisconsin Heart Disease and Stroke Prevention Program, Wisconsin Department of Health Services, http://www.dhs.wisconsin.gov/publications/p0/p00623.pdf, last accessed Oct. 13, 2014.

* cited by examiner

METHOD OF ASSESSING THE RELIABILITY OF A BLOOD PRESSURE MEASUREMENT AND AN APPARATUS FOR IMPLEMENTING THE SAME

CROSS REFERENCE TO RELATED APPLICATIONS

This application is the U.S. National Phase application under 35 U.S.C. § 371 of International Application No. PCT/EP2016/082367, filed Dec. 22, 2016, published as WO 2017/109064 on Jun. 29, 2017, which claims the benefit of European Patent Application Number 15202305.7 filed Dec. 23, 2015. These applications are hereby incorporated by reference herein.

TECHNICAL FIELD OF THE INVENTION

The invention relates to the field of measurements of blood pressure of a subject, and in particular relates to a method of assessing the reliability of a blood pressure measurement and an apparatus for implementing the same.

BACKGROUND TO THE INVENTION

Non-invasive arterial blood pressure (NIBP) is usually measured by slowly varying the pressure in a cuff that is wrapped around the upper arm of a subject. The NIBP is determined either by measuring sound distal from the cuff (known as the auscultatory method, based on Korotkoff sounds) or by measuring pressure pulsations in the cuff caused by volume pulsations of the arm and brachial artery and extracting features from the envelope of these pressure pulses (known as the oscillometric method). The oscillometric method is easily automated and is widely used. However, the auscultatory method is the "gold standard" for cuff based NIBP measurements.

The blood pressure (BP) of a subject is a dynamic value and is easily influenced by changes in a person's emotional and/or physiological state, in particular by pain, stress, discomfort and/or anxiety. During a BP measurement these factors can, sometimes unknowingly, raise blood pressure, resulting in false-high BP measurements without these external factors being identified as the cause of the high measurement of BP. These variations can be significant, and may result in an inappropriate diagnosis of hypertension. Overestimation of BP has implications in terms of therapy (for example a blood pressure measurement greater than 140/90 mmHg is diagnosed as hypertension and requires pharmacological therapy) and should be avoided in all cases, as it is both a symptom to be treated, but moreover a pivotal determinant in several long-term health risk analyses.

The uncertainty of the value of a BP measurement without proper context information is exemplified in several clinical protocols. By example, in the current Dutch GP standards (NHG), hypertension should only be the diagnosis if the BP is elevated during several consecutive measurements over the course of several weeks or months, or after a 24 hour ambulatory BP measurement.

Elderly people often experience pain/discomfort during the sudden increase in cuff pressure, and during the often prolonged cuff inflation time in case of poor measurements. Measurements can take as long as a minute to complete, and are often repeated due to unreliable results. The sensation of pain/discomfort can significantly increase the measured BP, thus the BP measurement does not reflect the true BP values of the patients.

In addition, many people experience anxiety while in the doctors' office. White coat hypertension, white coat syndrome, and masked hypertension are terms that are used to describe this phenomenon of BP increase due to anxiety. Research shows that such effects are very common and may account for up to 33% of diagnoses of hypertension. Research has shown that the white-coat effect can sometimes be mitigated by repeating the BP measurement after a few minutes, by the same or a different person (for example it has been seen that a doctor may measure a higher BP for a subject than a nurse). However, since the diagnosis of high blood pressure leads to pharmacological intervention, it is important to ensure that the measurements of blood pressure of the subject used in making this diagnosis properly reflect the long-term blood pressure of the subject.

Document US 2015/057554 A1 discloses method for monitoring blood pressure that comprises receiving one or more signals representative of one or more patient parameters, wherein at least one of the one or more signals comprises a plethysmography signal; determining a change in a pulse shape metric of the plethysmography signal; and determining a change in a blood pressure signal over a period of time based on the one or more signals. The method further comprises determining a confidence level of the blood pressure signal based at least in part on a correlation between the change in the blood pressure signal and the change in the pulse shape metric over the period of time.

In addition, US 2010/249556 A1 relates to systems and methods for monitoring pain management using measurements of physiological parameters based on a plethysmography signal. A reference physiological parameter may be compared against a later measurement to identify a change in condition that may indicate a pain management problem.

On the other hand, document US 2008/287814 A1 describes a technique for determining high-quality blood pressure values of a patient, especially in cases of unsupervised blood pressure measurements in a home environment. Such technique involves: determining the blood pressure of a patient using a blood pressure measuring device for measuring a blood pressure value; measuring, using an auxiliary device, the motor activity of the patient during a defined period of time prior to the blood pressure measurement; obtaining, using a processing device, the motor activity information and the blood pressure value; automatically assessing the blood pressure value using the motor activity information and said processing device; and providing a measuring result depending on the result of the assessment.

Therefore, there is a need for a way to assess the reliability of a blood pressure measurement.

SUMMARY OF THE INVENTION

As noted above, a limitation of blood pressure (BP) measurements is that they cannot be placed in the correct context, i.e. it is not possible to determine whether a BP measurement reflects the true value at that day or time or whether there are circumstantial factors that have affected the measurement.

With current BP measurement practices (i.e. with current methods and devices), it is difficult to evaluate whether a high blood pressure measurement is a sign of long-term hypertension or a temporary effect resulting from discomfort such as pain or anxiety. This problem is currently circumvented by requiring several (high) blood pressure measurements before a diagnosis can be made. However, this approach is not ideal, since temporary BP increases due to pain or anxiety during the measurement process may be systematically present during BP measurements. To overcome the problem of overdiagnosis of hypertension caused by these types of high BP measurements, it would be highly valuable to have a measure of whether a blood pressure measurement is reliable.

Therefore, according to a first aspect of the invention, there is provided a method of assessing the reliability of a measurement of blood pressure of a subject, the method in a control unit of an apparatus comprising: obtaining a first measurement of at least one physiological characteristic of the subject that is indicative of the level of pain and/or stress of the subject, wherein the first measurement is made prior to a measurement of blood pressure being made; obtaining the measurement of blood pressure of the subject; obtaining a second measurement of the at least one physiological characteristic of the subject, wherein the second measurement is made after the measurement of blood pressure is made and prior to a subsequent measurement of blood pressure being made; and determining if the measurement of blood pressure is reliable based on the first measurement and the second measurement.

In the context of the present invention, a measurement of blood pressure is regarded as not being reliable if the measurements of the physiological characteristic indicate that the blood pressure of the subject may have been affected by stress and/or pain during the blood pressure measurement.

Also in the context of the present invention the term pain should be understood as including discomfort and, similarly, the term stress should be understood as including anxiety and/or alertness.

The step of determining if the measurement of blood pressure is reliable comprises determining that the measurement of blood pressure is reliable if the first measurement of the at least one physiological characteristic and the second measurement of the at least one physiological characteristic indicate a low level of pain and/or stress.

In some embodiments, the step of determining if the measurement of blood pressure is reliable comprises determining that the measurement of blood pressure is not reliable if at least one of the first measurement of the at least one physiological characteristic and the second measurement of the at least one physiological characteristic indicate a high level of pain and/or stress.

In some embodiments, the step of determining if the measurement of blood pressure is reliable comprises determining that the measurement of blood pressure is not reliable if the first measurement of the at least one physiological characteristic and the second measurement of the at least one physiological characteristic indicate a different level of pain and/or stress prior to the measurement of blood pressure being made to the level of pain and/or stress indicated after the measurement of blood pressure is made.

In some embodiments, the first measurement of the at least one physiological characteristic and the second measurement of the at least one physiological characteristic indicate a different level of pain and/or stress if the first measurement and the second measurement differ by more than a threshold amount.

In some embodiments, the method further comprises the step of repeating the steps of obtaining if the measurement of blood pressure is not determined to be reliable. In some embodiments, the steps of obtaining are repeated until a measurement of blood pressure is obtained that is determined to be reliable.

In some embodiments, the step of obtaining a measurement of blood pressure of the subject is performed if (i.e., only if) the first measurement of the at least one physiological characteristic indicates a low level of pain and/or stress.

In some embodiments, if the first measurement of the at least one physiological characteristic indicates a high level of pain and/or stress, the method further comprises the step of obtaining one or more further measurements of the at least one physiological characteristic of the subject, wherein the one or more further measurements are made prior to the measurement of blood pressure being made; and wherein the step of obtaining a measurement of blood pressure of the subject is performed once a further measurement is made that indicates a low level of pain and/or stress.

In some embodiments, the method further comprises the step of outputting the measurement of blood pressure if it is determined to be reliable. In alternative embodiments, the method further comprises the step of outputting the measurement of blood pressure and an indication of whether the measurement of blood pressure is reliable.

In some embodiments, the at least one physiological characteristic is one or more of skin conductance and heart rate variability.

In some embodiments, the steps of obtaining comprise obtaining the first measurement, the second measurement and/or the measurement of blood pressure from a memory unit in the apparatus.

In alternative embodiments, the steps of obtaining comprise obtaining the first measurement and the second measurement from a physiological characteristic sensor that measures the at least one physiological characteristic of the subject, and obtaining the measurement of blood pressure from a blood pressure measurement device that measures the blood pressure of the subject.

According to a second aspect, there is provided a computer program product comprising a computer readable medium, the computer readable medium having computer readable code embodied therein, the computer readable code being configured such that, on execution by a suitable computer or processor, the computer or processor is caused to perform any of the methods described above.

According to a third aspect, there is provided an apparatus for assessing the reliability of a measurement of blood pressure of a subject, comprising a control unit configured to: obtain a first measurement of at least one physiological characteristic of the subject that is indicative of the level of pain and/or stress of the subject, wherein the first measurement is made prior to a measurement of blood pressure being made; obtain the measurement of blood pressure of the subject; obtain a second measurement of the at least one physiological characteristic of the subject, wherein the second measurement is made after the measurement of blood pressure is made and prior to a subsequent measurement of blood pressure being made; and determine if the measurement of blood pressure is reliable based on the first measurement and the second measurement.

The control unit is configured to determine that the measurement of blood pressure is reliable if the first measurement of the at least one physiological characteristic and the second measurement of the at least one physiological characteristic indicate a low level of pain and/or stress.

In some embodiments, the control unit is configured to determine that the measurement of blood pressure is not reliable if at least one of the first measurement of the at least one physiological characteristic and the second measurement of the at least one physiological characteristic indicate a high level of pain and/or stress.

In some embodiments, the control unit is configured to determine that the measurement of blood pressure is not reliable if the first measurement of the at least one physiological characteristic and the second measurement of the at least one physiological characteristic indicate a different level of pain and/or stress prior to the measurement of blood pressure being made to the level of pain and/or stress indicated after the measurement of blood pressure is made.

In some embodiments, the control unit is configured to determine that the first measurement of the at least one physiological characteristic and the second measurement of the at least one physiological characteristic indicate a different level of pain and/or stress if the first measurement and the second measurement differ by more than a threshold amount.

In some embodiments, the control unit is further configured to repeat the obtaining if the measurement of blood pressure is not determined to be reliable. In some embodiments, the control unit is further configured to repeat the obtaining until a measurement of blood pressure is obtained that is determined to be reliable.

In some embodiments, the control unit is configured to obtain the measurement of blood pressure of the subject if (i.e., only if) the first measurement of the at least one physiological characteristic indicates a low level of pain and/or stress.

In some embodiments, the control unit is further configured to obtain one or more further measurements of the at least one physiological characteristic of the subject if the first measurement of the at least one physiological characteristic indicates a high level of pain and/or stress, wherein the one or more further measurements are made prior to the measurement of blood pressure being made; and wherein the control unit is configured to obtain a measurement of blood pressure of the subject once a further measurement is made that indicates a low level of pain and/or stress.

In some embodiments, the control unit is further configured to output the measurement of blood pressure if it is determined to be reliable. In some embodiments, the control unit is configured to output the measurement of blood pressure and an indication of whether the measurement of blood pressure is reliable.

In some embodiments, the at least one physiological characteristic is one or more of skin conductance and heart rate variability.

In some embodiments, the control unit is configured to obtain the first measurement, the second measurement and/or the measurement of blood pressure from a memory unit in the apparatus. In alternative embodiments, the control unit is configured to obtain the first measurement and the second measurement by controlling a physiological characteristic sensor to measure the at least one physiological characteristic of the subject, and to obtain the measurement of blood pressure by controlling a blood pressure measurement device to measure the blood pressure of the subject.

In some embodiments, the apparatus further comprises a physiological characteristic sensor for obtaining measurements of the at least one physiological characteristic.

In some embodiments, the apparatus further comprises a device for obtaining measurements of the blood pressure of the subject. In some embodiments, the device comprises an inflatable cuff for use around a limb of the subject; a pump for inflating the cuff; and a pressure sensor for measuring the air pressure inside the inflatable cuff.

In some embodiments, the inflatable cuff comprises a physiological characteristic sensor for obtaining measurements of the at least one physiological characteristic.

In some embodiments, the physiological characteristic is measured using first and second electrocardiogram, ECG, electrodes, and the inflatable cuff comprises the first ECG electrode, and the second ECG electrode is configured to be held in a hand of the subject.

In some embodiments, the apparatus further comprises an activation component for enabling the subject to start the measurement of the blood pressure, and wherein the activation component is configured to be held in the hand of the subject along with the second ECG electrode. In some of these embodiments, the activation component enables the user to start not only the measurement of the blood pressure but also the first measurement of the at least one physiological characteristic prior to the measurement of the blood pressure; while in some other of these embodiments, the activation component enables the user to start only the measurement of the blood pressure.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides a way to determine whether a blood pressure measurement is reliable, i.e. whether the blood pressure measurement is a reliable indicator of the subject's long-term blood pressure or whether the blood pressure measurement has been affected by the pain and/or stress levels of the subject before, during, or after the blood pressure (BP) measurement.

Figure 1:
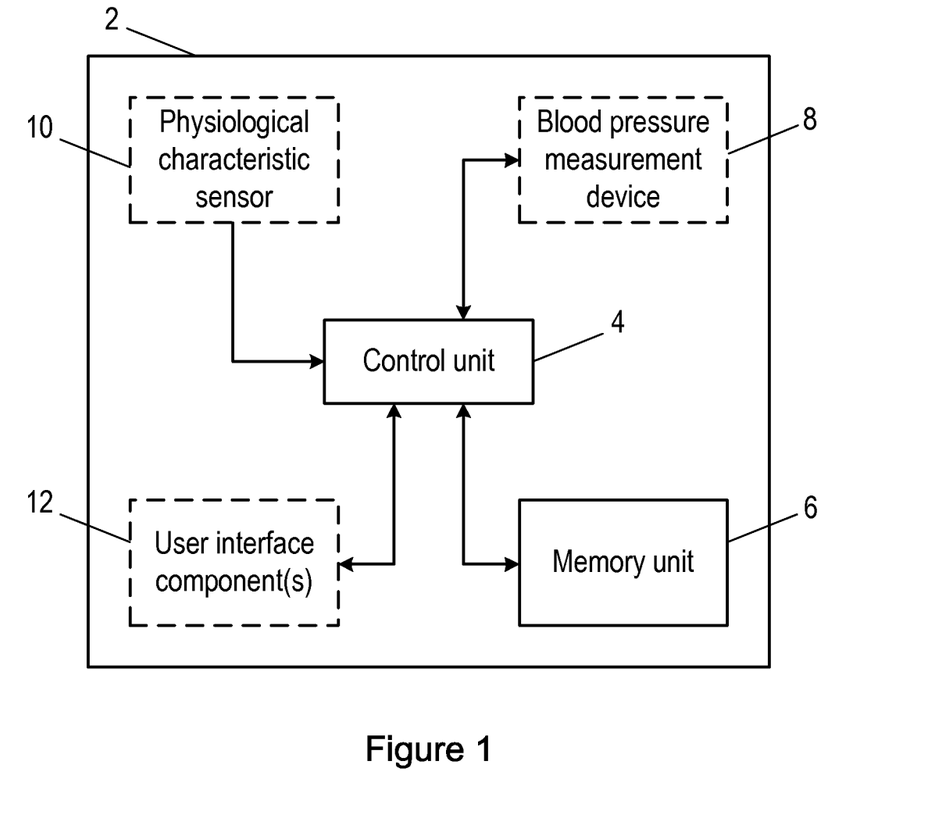
FIG. 1 is a block diagram of an apparatus according to an embodiment of the invention.

FIG. 1 shows a block diagram of an apparatus 2 according to an embodiment of the invention that can be used for assessing the reliability of a measurement of blood pressure. As described below, in some embodiments the apparatus 2 is, or is part of, an apparatus that measures the blood pressure of a subject, and in other embodiments the apparatus 2 can be separate from an apparatus or device that is used to measure the blood pressure of a subject. In those embodiments, the measurements of the blood pressure can be obtained by the separate device and provided to the apparatus 2 automatically (e.g. electronically via a wired or wireless connection), or via a manual input by the subject or another user of the apparatus 2.

The apparatus 2 comprises a control unit 4 that controls the operation of the apparatus 2 and that can implement the assessing method. Briefly, the control unit 4 is configured to determine if a measurement of blood pressure is reliable based on measurements of a physiological characteristic that are obtained shortly before and shortly after a blood pressure measurement. In other words, the control unit 4 is configured to use measurements of a physiological characteristic made or obtained before and after a blood pressure measurement to determine whether pain and/or stress of the subject may have affected the blood pressure of the subject during the blood pressure measurement.

The control unit 4 can comprise one or more processors, processing units, multi-core processors or modules that are configured or programmed to control the apparatus 2 to assess the reliability of a blood pressure measurement as described below.

In particular implementations, the control unit 4 can comprise a plurality of software and/or hardware modules that are each configured to perform, or are for performing, individual or multiple steps of the method according to embodiments of the invention.

The apparatus 2 comprises a memory unit 6 that can be used for storing program code that can be executed by the control unit 4 to perform the method described herein. The memory unit 6 can also be used to store signals and measurements made or obtained by any sensors (including a blood pressure measurement device 8 and/or a physiological characteristic sensor 10) that are part of the apparatus 2 or that are external to the apparatus 2.

In some embodiments, the apparatus 2 comprises a blood pressure measurement device 8 for obtaining a measurement of the blood pressure of the subject. The blood pressure measurement device 8 can be any type of device that is able to measure the blood pressure of a subject automatically (e.g. without an operator being present with the subject) or manually (e.g. that requires the presence of an operator, such as a healthcare professional). For example, the device 8 can be a cuff-based device that operates to measure the blood pressure of the subject using the auscultatory or oscillometric methods. Alternatively the device 8 can be a cuff-based device that uses the volume-clamp method to measure blood pressure. Those skilled in the art will be aware of these and other types of devices (e.g. that do not use a cuff) that can be used to measure blood pressure.

Where the apparatus 2 comprises a blood pressure measurement device 8, the blood pressure measurement device 8 can comprise a cuff that is to be placed around a limb (e.g. arm) or digit (e.g. finger) of a subject, a pump that is for inflating the cuff to a desired pressure, and a pressure sensor for measuring the air pressure inside the cuff. The pump may also be configured to deflate the cuff to a desired pressure and/or the device 8 can comprise a valve that can be controlled to deflate the cuff. A processor or control unit in the device 8 (or alternatively the control unit 4) can analyse the measurements from the air pressure sensor and control the pump and/or valve to inflate and/or deflate the cuff accordingly to obtain a measurement of the blood pressure of the subject.

In some embodiments the apparatus 2 comprises a physiological characteristic sensor 10 for measuring a physiological characteristic of the subject. In other embodiments the apparatus 2 may obtain measurements of a physiological characteristic from a physiological characteristic that is separate from the apparatus 2. In either case, the physiological characteristic that is measured is a physiological characteristic that is affected by the level of pain (including discomfort) that the subject is experiencing, and/or the level of stress (including anxiety and/or alertness) that the subject is suffering, and that can be used as an indicator of whether a blood pressure measurement may be affected by the pain and/or stress level of the subject. The physiological characteristic should be a physiological characteristic that is affected by acute stress levels (e.g. white coat anxiety) rather than longer-term chronic stress such as work-related or private-life related stress. In some embodiments multiple physiological characteristics can be measured (by one or multiple physiological characteristic sensors 10).

In some embodiments, the physiological characteristic is heart rate variability, since the variability of a subject's heart rate is known to decrease when they are in pain or stressed. Heart rate variability (HRV) can be measured using any type of physiological characteristic sensor 10 that can measure the heart rate of a subject. Those skilled in the art will be aware of various ways in which HRV can be derived from a measurement signal. Preferably the HRV variability is calculated from a measured physiological signal such as ECG or PPG. Different HRV variability calculations can be considered individually or in combination with each other. Some HRV measures that can be considered include the following: (i) measures calculated from a frequency domain analysis of the corresponding physiological characteristic signal, such as low frequency power, high frequency power, very low frequency power, ratio of low frequency to high frequency power, very low frequency, low frequency and high frequency powers normalized based on total power, or based on power in a specific band; (ii) measures calculated from a time domain analysis of the collected signals, such as standard deviation or variability of peak to peak distances, percentage of peak to peak distances that exceed a certain threshold. The HRV can be determined by the control unit 4 or by another processor or control unit associated with the sensor 10.

In these embodiments the physiological characteristic sensor 10 can be an accelerometer that is located on the subject's chest or back (with the acceleration measurement signal being processed to identify accelerations/movements due to the beating of the heart), a microphone that is located on the subject's chest or back (with the sound measurement signal being processed to identify sounds that occur due to the beating of the heart) or a photoplethysmogram (PPG) or blood oxygenation (SpO2) sensor. In an alternative embodiment, which is described in more detail below with reference to FIG. 4, the physiological characteristic sensor 10 can be a microphone that is used in combination with an inflatable cuff and that measures Korotkoff sounds that are created by partial occlusion of an artery by the cuff. The heart rate, and thus the heart rate variability is determined from an analysis of the Korotkoff sounds.

In preferred embodiments, the physiological characteristic sensor 10 is an electrocardiogram (ECG) sensor that obtains a signal representing the electrical activity of the subject's heart. An ECG sensor is preferred as it generally provides a higher measurement resolution than other types of heart rate sensors (e.g. those types described above) and enables a better detection of the changes in heart rate variability that occur with varying pain and/or stress levels of a subject. Although an ECG sensor can require the use of up to ten electrodes to obtain a full ECG signal (the use of which can itself induce white coat hypertension), as only heart rate information is required the ECG sensor preferably only comprises just two electrodes that are located either side of the subject's heart (e.g. located on each arm). More details of a preferred embodiment that comprises an unobtrusive ECG sensor 10 are provided below with reference to FIG. 3.

In some embodiments, the physiological characteristic is skin conductivity, also known as galvanic skin response, since the conductivity of a subject's skin is known to increase when they are in pain or stressed (e.g. due to changes in the excretion of sweat by the skin). Skin conductance can be measured using a pair of electrodes that are placed in contact with the subject's skin. An electrical current may be applied through one of the electrodes and the resistance of the skin measured, or the voltage between the electrodes can be measured. In an exemplary embodiment, the electrodes can be configured to be in contact with the skin on the palm of a hand of the subject. An increase in the skin conductivity (consistent with an increase in stress and/or pain) can be observed as an increase in level and/or an increase in the number of peaks in the skin conductivity signal, an increase in the amplitude of the peaks in the signal, and/or peaks with a shorter rise time, etc.

In some embodiments both HRV and skin conductivity can be measured, and the measurements analysed to determine whether pain and/or stress may have affected a blood pressure of the subject during a blood pressure measurement.

Those skilled in the art will be aware of other types of physiological characteristic that can be used as a measure of the level of stress and/or pain experienced by a subject. In particular, heart rate variability and skin conductance are under the control of the same parasympathetic/sympathetic balance in the nervous system, and any other physiological characteristic that is subject to the same balance control can be measured and used as an indicator of the stress and/or pain of a subject—for example pupil size, dryness of mouth, etc. Other physiological characteristics that can be measured and analysed to determine a measure of the level of stress and/or pain of the subject can include brain activity, breathing rate, muscle activity and skin temperature.

The measurements of the physiological characteristics and the blood pressure measurements can be processed generally as the measurements are made or obtained (e.g. in real-time or near-real time), or they can be stored in the memory unit 6 and the control unit 4 can retrieve and process the previously-made measurements from the memory unit 6 at a later time.

As suggested above, it will be appreciated that the output of the physiological characteristic sensor 10 may be a time series of values for the physiological characteristic, or 'raw' measurements (e.g. measurements of heart rate, or an ECG signal) that are processed by the control unit 4 in order to determine a time series of values for the physiological characteristic.

In some embodiments the control unit 4 (and thus the apparatus 2) may be part of a smart phone or other general purpose computing device that can comprise, be connected to or otherwise receive a measurement signal from a physiological characteristic sensor 10 and a blood pressure measurement device 8, but in other embodiments, as noted above, the apparatus 2 can be an apparatus that is dedicated to the purpose of measuring the blood pressure of a subject. In embodiments where the control unit 4 is part of a smart phone or other general purpose computing device, then depending on the physiological characteristic to be monitored, the sensor 10 could be a sensor that is integrated into the smart phone, or a sensor that is separate to the smart phone and that can provide sensor signals/measurements to the smart phone/computing device for processing and analysis (for example via a wired or wireless connection).

It will be appreciated that FIG. 1 only shows the components required to illustrate this aspect of the invention, and in a practical implementation the apparatus 2 will comprise additional components to those shown. For example, the apparatus 2 may comprise a battery or other power supply for powering the apparatus 2 or means for connecting the apparatus 2 to a mains power supply, and/or a communication module for enabling the measurements of the physiological characteristic, measurements of the blood pressure of the subject and/or an indication of the reliability of a blood pressure measurement to be communicated to a base unit for the apparatus 2 or to a remote computer (e.g. that is operated by a healthcare professional). The apparatus 2 may also comprise at least one user interface component 12 that is for use in providing the subject or other user of the apparatus 2 (for example a family member or healthcare provider) with information resulting from the method according to the invention. For example the user interface component can provide an indication of the measured blood pressure, along with an indication of whether the blood pressure measurement is reliable (e.g. an indication of whether the measurement been affected by stress and/or pain experienced by the subject). The user interface component can comprise any component that is suitable for providing the above information, and can be, for example, any one or more of a display screen or other visual indicator, a speaker, one or more lights, and a component for providing tactile feedback (e.g. a vibration function).

In addition, the user interface component 12 is or can comprise some means that enables the subject or another user of the apparatus 2 to interact with and/or control the apparatus 2. For example, the user interface component could comprise a switch, a button or other control means for activating and deactivating the apparatus 2 and/or the measurement and/or assessment process.

Figure 2:
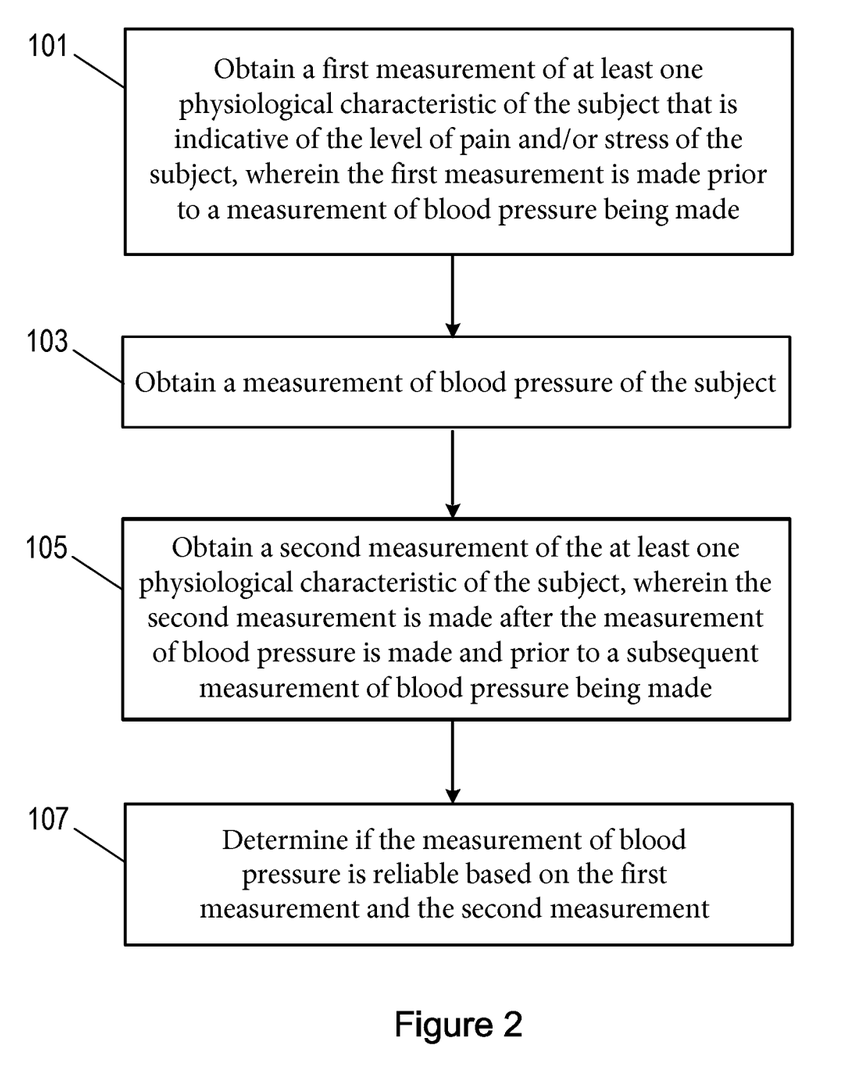
FIG. 2 is a flow chart illustrating a method performed in a control unit of an apparatus according to an embodiment of the invention.

FIG. 2 illustrates a method of assessing the reliability of a measurement of blood pressure of a subject according to an embodiment of the invention. This method can generally be performed by or under the control of control unit 4.

In a first step, step 101, a first measurement of a physiological characteristic of the subject is obtained. The physiological characteristic is a physiological characteristic that is affected by the level of pain and/or stress that the subject is experiencing at the time of the measurement. The first measurement can be obtained directly using or from a physiological characteristic sensor 10 (in which case the physiological characteristic sensor 10 is used to make a measurement of the physiological characteristic), or it can be retrieved from memory unit 6, and 'obtaining' a measurement should be understood accordingly. As noted above, the output of the physiological characteristic sensor 10 may be a time series of values for the or a physiological characteristic, or 'raw' measurements (e.g. acceleration measurements or an ECG signal). In the latter case, step 101 may comprise processing the raw measurements to determine measurements of the physiological characteristic. In preferred embodiments the physiological characteristic(s) can be heart rate variability and/or skin conductivity, although other or further physiological characteristics can be measured.

Whether the control unit 4 controls a physiological characteristic sensor 10 to make a measurement of the physiological characteristic at that time or whether the control unit 4 retrieves a measurement from memory unit 6, the first measurement is made prior to the making of a measurement of the blood pressure of the subject (i.e. prior to the measurement of the blood pressure that is to be assessed for reliability). The first measurement may be made immediately prior to the blood pressure measurement being made (e.g. immediately before the inflation of a cuff is initiated), or it may be made a predetermined time period (e.g. a few seconds or a few minutes) before the blood pressure measurement is made.

Next, in step 103, a measurement of the blood pressure of the subject is obtained. As with step 101, 'obtaining' a measurement can comprise controlling a blood pressure measurement apparatus 8 to make a measurement of blood pressure after the first measurement of the physiological characteristic has been made in step 101, or it can comprise retrieving a measurement of blood pressure that was made previously from a memory unit 6.

Next, in step 105, a second measurement of the physiological characteristic is obtained. Also as with step 101, 'obtaining' can comprise controlling a physiological characteristic sensor 10 to make a measurement of the physiological characteristic, or retrieving a previously-made measurement from memory unit 6. This second measurement is made after the measurement of blood pressure of the subject in step 103 and prior to a subsequent measurement of blood pressure being made. The second measurement may be made immediately after the blood pressure measurement is made (e.g. immediately after the cuff is (completely) deflated), or it may be made a few seconds or a few minutes after the blood pressure measurement is made, but before a subsequent measurement of blood pressure is started.

Then, in step 107, the control unit 4 determines if the measurement of blood pressure is reliable based on the first measurement of the physiological characteristic and the second measurement of the physiological characteristic. That is, the control unit 4 determines whether the measurements of the physiological characteristic indicate that the blood pressure of the subject may have been affected by stress and/or pain during the blood pressure measurement.

Although not shown in FIG. 2, in some embodiments, after step 107 the blood pressure measurement can be output to the subject or other interested party (e.g. a healthcare professional), for example via a display 12 on the apparatus 2, along with an indication of the reliability of the blood pressure measurement (e.g. an indication of the measurement being reliable or unreliable). In other embodiments, after step 107, the blood pressure measurement may only be output to the subject or other interested party if the measurement is considered to be reliable.

In some embodiments, if the blood pressure measurement is determined to be unreliable in step 107, further blood pressure measurements can be made until a measurement is obtained that is determined to be reliable or until a certain number of blood pressure measurements have been made (e.g. 5). That is, after step 107, steps 103 and 105 can be repeated to obtain a new blood pressure measurement and (second) measurement of the physiological characteristic after the blood pressure measurement is obtained, and step 107 can be performed for the new blood pressure measurement based on the physiological characteristic measurements from prior to and after the new blood pressure measurement. Steps 103 and 105 (and 107) may not be repeated immediately after determining that the previous blood pressure measurement is unreliable, but instead there may be a time interval (of, for example, a few minutes) to allow the subject to relax (e.g. reduce their stress level) before steps 103 and 105 are performed. In that case, step 101 may also be repeated before step 103 to obtain a new measurement of the stress and/or pain level of the subject before the blood pressure measurement is made. These embodiments are particularly advantageous for obtaining reliable measurements of blood pressure using an automated blood pressure measurement device that can be used in the subject's home or otherwise without the supervision of a doctor or other healthcare professional.

A blood pressure measurement can be determined to be reliable in step 107 if the first and second measurements both indicate a low level of pain and/or stress. As described below, a low level may be determined with reference to a threshold value, which can be derived from physiological characteristic measurements for a population of subjects, or from previous physiological characteristic measurements and pain/stress assessments for that particular subject. It will be appreciated that the first and second measurements do not need to be the same as each other in order for a low level to be indicated. It will also be appreciated that a 'low' level of stress and/or pain may be considered as a 'normal' level of stress and/or pain for the subject.

In some embodiments, a blood pressure measurement can be determined to be unreliable in step 107 if one or both the first and second measurements indicate a high level of pain and/or stress in the subject. It will be appreciated that the first and second measurements do not need to be the same as each other in order for a high level to be indicated. In this embodiment (which may be combined with the 'low level' embodiment above), a high level of pain and/or stress can be identified by comparison of the first and second measurements to a threshold. It will be appreciated that there can be a single threshold that is used to distinguish between low and high levels of stress and/or pain, or there can be respective thresholds for determining if a measurement corresponds to a low or high level of stress and/or pain. Again, the threshold values can be derived from physiological characteristic measurements for a population of subjects, or from previous physiological characteristic measurements and pain/stress assessments for that particular subject.

In some embodiments (which can be separate from or combined with the above embodiments), a blood pressure measurement can be determined to be unreliable in step 107 if there is a change in the stress and/or pain level during the measurement of the blood pressure (i.e. if the first and second measurements of the physiological characteristic indicate different stress and/or pain levels before and after the blood pressure measurement). In this embodiment, it will be appreciated that for a change in the stress and/or pain level to be identified, the first and second measurements may need to differ by more than a threshold amount. For example, if the measurements of the physiological characteristic are normalised (as described below), the first and second measurements made need to differ by more than 20, 30, 40 or even 50% for the measurements to indicate a change in the stress and/or pain level. Alternatively, in this embodiment the control unit 4 can determine if each of the first and second measurements correspond to a low or high level of stress and/or pain, and a change in the stress and/or pain level can be identified if one of the first and second measurements indicates a low level and the other of the measurements indicates a high level.

As noted above, in some embodiments the physiological characteristic measurements are analysed to determine if they indicate high or low levels of stress and/or pain by comparison by one or more thresholds. In these embodiments the physiological characteristic measurements (e.g. measurements of HRV and skin conductance/conductivity) can be normalised so that they can be compared across populations and across different days (for the same subject).

Some exemplary ways of defining low and high pain and/or stress levels are set out below:

Baseline data for a subject can be collected when the subject is relaxed (e.g. in their own home, when a blood pressure measurement is not scheduled or due to be taken, etc.), and if a measurement of the physiological characteristic exceeds the baseline by certain amount (e.g. by a certain percentage, such as 20, 30, 40 or 50%), then the measurement can be considered as indicating a high level of stress and/or pain. If a measurement does not exceed the baseline by the certain amount, the measurement can be considered as indicating a low level of stress and/or pain.

In a similar way, a baseline can be established based on a population of subjects (e.g. all subjects, subjects of a similar age, the same gender, the same morbidities, similar medications, etc.), and the measurements of the physiological characteristic can be compared against the population baseline (if the measurements are normalised).

In some embodiments, the analysis of the measurements of the physiological characteristic in step 107 to determine if either indicates that the subject is experiencing a high level of pain and/or stress can make use of a machine learning approach (e.g. that use a decision tree, a neural network, etc.). These approaches are particularly useful when multiple physiological characteristics are measured, as they can provide a decision on whether the subject is experiencing pain and/or stress when only one of the physiological characteristic measurements is abnormal. For example it may provide a 'high' decision if there is an increase in HRV that would by itself indicate stress, even if the skin conductance is lower. Of course, if both measurements indicate stress and/or pain then the confidence in the 'high' output will be higher.

Similarly in some embodiments a data mining approach can be used to classify whether particular measurements of the physiological characteristic correspond to a high level of pain and/or stress. In this approach physiological characteristic measurements that are representative of various stressful and/or painful conditions can be collected, and this data can be used to train classifier which later can be used to determine if a new physiological characteristic measurement translates into a low stress/pain condition which is acceptable for making BP measurements, or into a high stress/pain condition which may affect the reliability of BP measurements. It will be appreciated that when the data mining approach is used, the physiological characteristic measured before the BP measurement and the physiological characteristic measured after the BP measurement do not have to be the same type of physiological characteristic (although it is preferred they are the same type of physiological characteristic) since the classifier can account for different types of parameter sets.

In embodiments where step 107 determines a blood pressure measurement to be unreliable if there is a change in the stress and/or pain level during the measurement of the blood pressure, the data mining approach can be used, and the change can be defined in terms of a change in the condition that the classifier outputs (e.g. a change from an output of high stress to low stress, or vice versa), or in terms of a change in the confidence value for the output of the classifier (in case the outputs before and after are in the same category, e.g. both low stress).

Table 1 below indicates some exemplary variations in the stress and/or pain level before and after a blood pressure measurement and the corresponding reliability indications that can be determined in step 107, along with a suggestion for whether the measurement of blood pressure should be repeated (e.g. if the measurement is deemed unreliable). In Table 1, the 'normal' and 'high' indications for the blood pressure can be obtained by a comparison of the blood pressure measurement with clinically defined normal and high values of blood pressure.

TABLE 1

| First measurement (stress/pain level) | BP measurement | Second measurement (stress/pain level) | Decision | Suggestion |
| --- | --- | --- | --- | --- |
| Low | Normal | Low | Reliable, healthy | Measurement is okay |
| Low | High | Low | Reliable, hypertension | Measurement is okay |
| Low | Normal | High | Probably healthy, pain/discomfort | Repeat measurement |
| Low | High | High | Unreliable, pain/stress | Repeat measurement |
| High | Normal | Low | Probably healthy, initial anxiety | Repeat measurement |
| High | High | Low | Unreliable, initial anxiety | Repeat measurement |
| High | Normal | High | Probably healthy, initial anxiety | Repeat measurement |
| High | High | High | Unreliable, anxiety | Repeat measurement |

Thus it can be seen from the example in Table 1 that the blood pressure measurement is considered reliable and no repetition of the method is suggested when the stress and/or pain level is considered to be low before and after the blood pressure measurement. In all other cases (i.e. where the stress and/or pain level is considered to be high before and after the blood pressure measurement is made, and where the stress and/or pain level changes across the blood pressure measurement), the blood pressure measurement is considered to be unreliable (even where the blood pressure measurement indicates a 'normal' blood pressure).

In a similar way, if the physiological characteristic measurement prior to the blood pressure measurement is 'normal' (i.e. not indicative of a high stress and/or pain level) and remains within limits after the blood pressure measurement (e.g. the change in the physiological characteristic measurement value is <30%), it can be determined that the blood pressure measurement is unlikely to have been affected by pain/anxiety/discomfort and can be classified as "reliable". If the physiological characteristic measurement prior to the blood pressure measurement is normal, an increase in stress levels as indicated by the physiological characteristic measurement after the blood pressure measurement (e.g. a change of more than 30%) is an indicator of pain or discomfort for the subject during the measurement, and the blood pressure measurement is considered as unreliable.

In some embodiments, if the physiological characteristic measurement prior to the blood pressure measurement indicates a high stress and/or pain level, this is suggestive of anxiety, and the subsequent blood pressure measurement can be considered unreliable. In that case, the physiological characteristic measurement after the blood pressure measurement can, in some cases, be considered irrelevant since it is the initial measurement of the physiological characteristic that determines the reliability of the blood pressure measurement.

In view of this, in some embodiments before a blood pressure measurement is obtained in step 103, the first measurement of the physiological characteristic obtained in step 101 can be analysed to determine if it indicates a high level of pain and/or stress. If the measurement does indicate a high level of pain and/or stress, the method can comprise obtaining one or more measurements of the physiological characteristic, and then only performing step 103 (and the subsequent steps) once a further measurement of the physiological characteristic is obtained that indicates a low level of pain and/or stress. The further measurements of the physiological characteristic may be made on a regular basis, for example, after a few seconds or minutes from the previous measurement. Thus, this embodiment effectively enables the selection or identification of an appropriate time for the blood pressure measurement to be made, and avoids making unnecessary blood pressure measurements (that, for example, involve the inflation of a cuff and associated discomfort for the subject). This embodiment is particularly suited to automated blood pressure measurement devices that operate to automatically measure blood pressure without requiring the presence of a doctor or other healthcare professional.

For example, in an embodiment where both heart rate variability (HRV) and skin conductance measurements (SCR) are made, when a blood pressure measurement is scheduled or due to be made, a first measurement of SCR and HRV is taken. The first measurement of each physiological characteristic indicates a high pain and/or stress level, in which case the blood pressure measurement is delayed until a HRV and SCR measurement is obtained that indicates a low level of pain and/or stress. A second measurement of each physiological characteristic may be taken some time later (e.g. 5 minutes), and this also indicates a high level of pain and/or stress, so the measurement of blood pressure is again delayed. If a third measurement taken some time later (e.g. 5 minutes) indicates a low level of pain and/or stress, then the blood pressure measurement can be made, followed by a measurement of HRV and SCR after the blood pressure measurement is made. This measurement of HRV and SCR is used to determine if the blood pressure measurement is reliable.

It will be appreciated that the above embodiment may be combined with the embodiment in which the measurement process in steps 101/103-107 is repeated if an unreliable blood pressure measurement is obtained. Thus, for example, a blood pressure measurement will only be initiated once a physiological characteristic measurement is made that indicates a low level of pain and/or stress, and the blood pressure measurement process will be repeated if an unreliable measurement of blood pressure is made (but the measurement is only repeated once a low level of pain and/or stress is measured).

Figure 3:
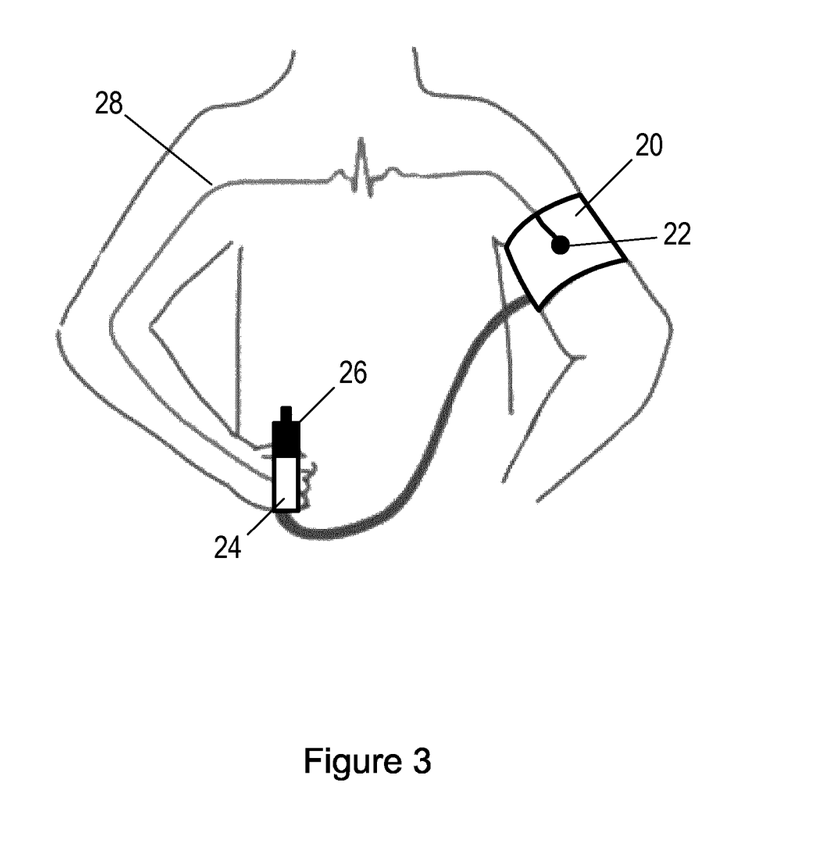
FIG. 3 is an illustration of an apparatus according to an exemplary embodiment being used by a subject.

A preferred embodiment of an apparatus 2 according to the invention is shown in FIG. 3. In this embodiment, blood pressure is measured using a conventional automated cuff-based measurement technique (e.g. that is based on the oscillometric method), and the physiological characteristic is heart rate variability that is measured from an ECG signal.

In particular, the blood pressure measurement device 8 in the apparatus 2 comprises a cuff 20 that can be inflated and deflated to occlude an artery in the subject's arm, a pressure sensor (not shown) that measures the air pressure inside the cuff (including pressure pulsations in the cuff caused by volume pulsations of the arm) and a pump (also not shown) that inflates the cuff to a desired pressure level.

A first ECG electrode 22 is included in the cuff 20 (for example on the inside edge of the cuff 20) so that it is in electrical contact with the skin of the subject before and after the blood pressure measurement is taken. A second ECG electrode 24 is included in a part 26 of the apparatus 2 that is held in the hand of the subject on the opposite side of the body to the arm that the cuff 20 is on so that the second ECG electrode 24 is in electrical contact with the skin on the hand of the subject. The electrodes 22, 24 are connected to control unit 4 (not shown). Thus, electrodes 22, 24 enable skin contact to be made at two points: underneath the cuff 20, and in the hand of the subject, which creates a circuit across the heart and enables an ECG signal to be obtained (as indicated by line 28).

When a blood pressure measurement is to be made, an HRV measurement is made prior to inflation of the cuff 20, cuff inflation then proceeds according to the conventional oscillometric measurement technique, followed by a second HRV measurement after the blood pressure measurement is obtained.

The embodiment of the invention shown in FIG. 3 is advantageous as it enables the ECG measurement to be obtained without the subject necessarily being aware that an ECG measurement is being made (which can itself cause anxiety in the subject).

In an alternative embodiment, the physiological characteristic can be skin conductance, and the skin conductance electrodes can be incorporated into the cuff 20 in a similar way to the first ECG electrode 22, or incorporated into the part 26 of the apparatus 2 that is held in a hand of the subject when the blood pressure measurement is to be made. Again, this embodiment is advantageous as the subject may be unaware that a measurement of skin conductance (and therefore stress/anxiety) is being made.

In a further embodiment, both HRV and skin conductance can be measured and used to assess the reliability of the blood pressure measurement. In this case, the HRV can be measured using an ECG signal as shown in FIG. 3, and skin conductance can be measured using one or more further electrodes that are incorporated into the cuff 20, or included in part 26 that includes the second ECG electrode 24.

In a further or alternative embodiment, the part 26 that is held by the subject may include a button, switch or other activation component that enables the subject to initiate the blood pressure measurement process. On pressing this button (or otherwise initiating the process), a measurement of the physiological characteristic is made and then the cuff 20 is inflated. This embodiment has the advantage that the subject should not be surprised (and therefore made anxious) by the cuff suddenly starting to inflate, since they will have initiated the measurement themselves.

Figure 4:
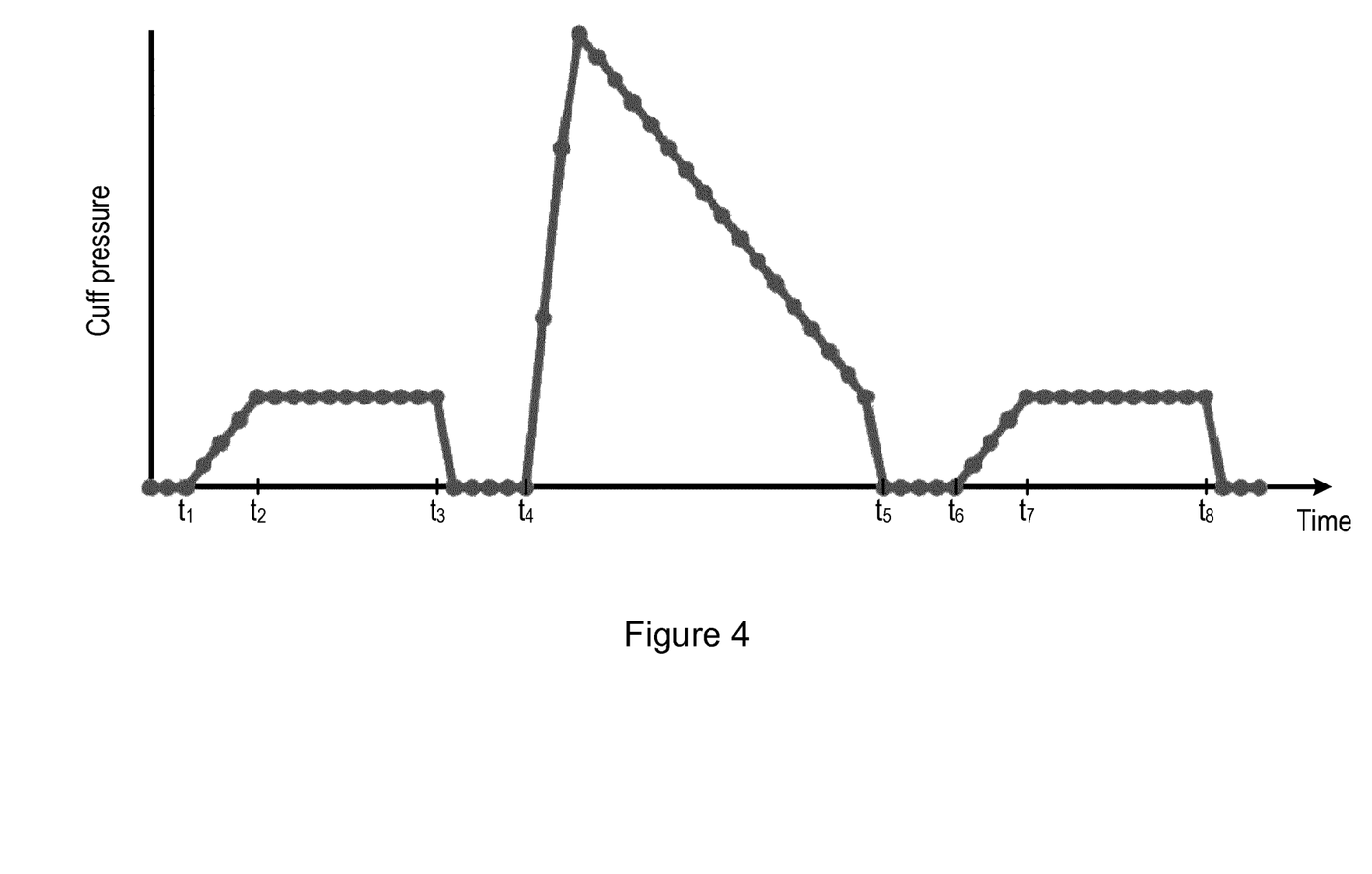
FIG. 4 is a graph illustrating the measurement of Korotkoff sounds for determining heart rate variability.

As noted above, in embodiments where the physiological characteristic is heart rate variability, the physiological characteristic sensor 10 can be a microphone that is used in combination with the inflatable cuff 20 to measure Korotkoff sounds that are created by partial occlusion of an artery with the cuff 20. These Korotkoff sounds are measured during a separate inflation procedure to the inflation procedure used to measure the blood pressure, as shown in FIG. 4. The heart rate, and thus also the heart rate variability is determined from an analysis of the Korotkoff sounds. Techniques for determining the heart rate and HRV from Korotkoff sounds are known in the art and will not be described further herein.

Referring to FIG. 4, an HRV measurement is initiated (e.g. corresponding to step 101) at a time $t_1$, in which inflation of the cuff 20 starts until Korotkoff sounds are first detected (time $t_2$). At time $t_2$, the inflation of the cuff 20 is stopped and the Korotkoff sounds are recorded using the microphone until sufficient sounds for determining HRV have been measured (indicated as time $t_3$). At time $t_3$ the HRV measurement (sound recording) stops and the cuff 20 is deflated. The standard blood pressure measurement can be performed at time $t_4$ in which the cuff 20 is inflated to a peak pressure sufficient to measure the diastolic and/or systolic blood pressure and then gradually deflated. Once the blood pressure measurement has been made, the cuff 20 is deflated (time $t_5$). Shortly after the blood pressure measurement is made, a second HRV measurement is initiated (e.g. corresponding to step 105) at a time $t_6$. The second HRV measurement is carried out in the same way as the first HRV measurement, and thus inflation of the cuff 20 is started at time $t_6$ until Korotkoff sounds are first detected (time $t_7$). At time $t_7$, the inflation of the cuff 20 is stopped and the Korotkoff sounds are recorded using the microphone until sufficient sounds for determining HRV have been measured (indicated as time $t_8$). At time $t_8$ the HRV measurement (sound recording) stops and the cuff 20 is deflated.

In further embodiments of the invention, the assessment of blood pressure measurements for reliability can be further improved by carrying out unobtrusive monitoring of the subject prior to the BP measurement (for example while the subject is in a doctor's waiting room, when the person is setting up the apparatus 2 in a home environment, or other), and during and shortly after the BP measurement.

If a BP measurement is distorted by a white-coat effect, the BP must have increased during a relatively short period prior to the BP measurement (e.g. as a result of subject anxiety). Whilst this short-term BP increase is difficult to detect by unobtrusive methods (i.e. without performing a BP measurement), it is often accompanied by several other signs that can be detected using unobtrusive methods. In particular, the way in which the human body achieves a rapid BP increase involves either a heart rate increase, a heart contraction force increase (increased stroke volume), or an increase in total vascular resistance. These increases can be detected using remote sensors (e.g. sensors that are not in direct contact with the subject), such as a camera, or sensors that are in contact with the subject, such as a PPG sensor, accelerometer, skin conductance sensor, etc. These sensors may be different to those used in the apparatus 2 to measure the physiological characteristic before and after the BP measurement, or they can be the same sensors (for example where the sensors are part of a different apparatus to the apparatus that is used to measure the blood pressure. A heart rate increase can be measured by unobtrusive methods, such as remote PPG sensing, a normal (i.e. requiring skin contact) PPG sensor, or a wearable accelerometer. Both an increase in the force of heart contractions and/or an increase in systemic resistance will cause a stronger pulse signal (amplitude), which can be measured using a wearable sensor such as an accelerometer or a PPG sensor. Another effect of anxiety may be increased sweating, which may be detected by measurement of skin conductance, e.g. using wearable devices as described above, or by using a camera.

As there are variations in both heart rate and the amplitude of the contraction within the population, the absolute values of heart rate and amplitude are not sufficient for this analysis, but a relative value e.g. an increase of heart rate and/or increase in signal amplitude in the waiting room can be detected. As an example, if an increase in heart rate is measured while the subject is in the waiting room, this can be used as an indicator of anxiety.

The measurements described above can be performed while the subject is in a waiting room prior to a doctor's visit that will include a BP measurement. Any changes in the described physiological signs during the waiting time can be interpreted as a symptom of white-coat hypertension, or used in the analysis in step 107 of a blood pressure measurement. This assessment can help the doctor to identify patients that have white-coat hypertension, so that they can adapt their procedures to account for the state of the subject. Taking the state of the subject into account may help in the accurate interpretation of BP measurements, and may avoid or reduce the occurrence of a false diagnosis of hypertension.

In further embodiments of the invention, information on the posture of the subject (or information on the posture of the part of the body of the subject at which the blood pressure measurement is to be obtained) can be used as an input for determining the timing and reliability of a blood pressure measurement. The (arm) posture, the level of back support, and the resting of the arm during the BP measurements can all influence the measured BP value, and in many cases increase the determined BP above the actual BP. Thus, in some embodiments, to further improve the quality of the BP measurements, one or more sensors, such as an accelerometer(s), gyroscope(s) and/or camera(s) may be used to assess the posture of the subject (or the posture of the arm of the subject) and determine whether the posture is optimal for obtaining a reliable BP measurement (irrespective of whether the subject is stressed and/or in pain). This assessment may be performed prior to the measurement of the blood pressure being made, in which case the measurement may be delayed or prevented until the correct posture is assumed by the subject (possibly in response to a prompt or alert from the apparatus 2 as to the occurrence of an incorrect posture, or a prompt or alert that indicates to the subject how to adopt the correct posture). Alternatively, the assessment of the posture can be taken into account in step 107 when the reliability of the BP measurement is determined.

In further embodiments of the invention, vocal cues and/or facial expressions of the subject can be assessed with the physiological characteristic measurement in step 107 to determine the level of pain and/or stress of the subject. In particular, the sounds and/or speech made by a subject can be used to reliably assess their emotions and mood. Analysis of facial expressions can be used in a similar way. These vocal cues and facial expressions can be used in the same manner as other physiological characteristic measurements, i.e., to assess the subject's state or level of pain and/or stress and accordingly control how the blood pressure measurements should be interpreted (i.e. reliable/unreliable). To make use of sound and/or face-based assessment of the subject before, during and after blood pressure measurements, it is necessary to obtain images of the face of the subject and recordings of the subject's voice. Thus, a microphone and/or camera can be provided, for example as part of the apparatus 2, or otherwise included in a room or other area in which a blood pressure measurement is to be made (e.g. a doctor's office), and the sounds and images provided to the control unit 4 for analysis. Those skilled in the art will be aware of numerous techniques for analysing recorded speech and/or images of a face to determine the emotional state of the subject, and further details are not provided herein.

There is therefore provided a method and apparatus for assessing the reliability of blood pressure measurements.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be

The invention claimed is:

1. An apparatus for assessing reliability of a measurement of blood pressure of a subject, comprising:
   a control unit configured to:
      obtain a first measurement of at least one physiological characteristic of the subject that is indicative of the level of pain and/or stress of the subject, wherein the first measurement is made prior to a measurement of blood pressure being made;
      obtain the measurement of blood pressure of the subject;
      obtain a second measurement of the at least one physiological characteristic of the subject, wherein the second measurement is made after the measurement of blood pressure is made and prior to a subsequent measurement of blood pressure being made; and
      determine if the measurement of blood pressure is reliable based on the first measurement and the second measurement, wherein the measurement of blood pressure is determined to be reliable if the first measurement of the at least one physiological characteristic and the second measurement of the at least one physiological characteristic indicate a low level of pain and/or stress;
   an inflatable cuff adapted to use around a limb of the subject;
   a pump to inflate the cuff; and
   a pressure sensor to measure air pressure inside the inflatable cuff, wherein the inflatable cuff further comprises a physiological characteristic sensor to obtain measurements of the at least one physiological characteristic, and wherein the physiological characteristic is heart rate variability or skin conductance/conductivity.

2. An apparatus as claimed in claim 1, wherein the control unit is configured to obtain the first measurement, the second measurement and/or the measurement of blood pressure from a memory unit in the apparatus.

3. An apparatus as claimed in claim 1, wherein the control unit is configured to obtain the first measurement and the second measurement by control of the physiological characteristic sensor to measure the at least one physiological characteristic of the subject, and to obtain the measurement of blood pressure by control of the inflatable cuff to measure the blood pressure of the subject.

4. An apparatus as claimed in claim 1, wherein the control unit is further configured to obtain one or more further measurements of the at least one physiological characteristic of the subject if the first measurement of the at least one physiological characteristic indicates a high level of pain and/or stress, wherein the one or more further measurements are made prior to the measurement of blood pressure being made; and wherein the control unit is configured to obtain a measurement of blood pressure of the subject once a further measurement is made that indicates a low level of pain and/or stress.

5. Apparatus as claimed in claim 1, wherein the physiological characteristic sensor of the inflatable cuff comprises a first ECG (electrocardiogram) electrode, and the apparatus further comprises a second ECG electrode configured to be held in a hand of the subject, the control unit being configured to obtain as the physiological characteristic measurement the heart rate variability of the subject measured using the first and second ECG electrodes.

6. Apparatus as claimed in claim 1, wherein the physiological characteristic sensor of the inflatable cuff comprises skin conductance electrodes, the control unit being configured to obtain as the physiological characteristic measurement skin conductivity/conductance of the subject measured using the skin conductance electrodes.

7. Apparatus as claimed in claim 5, wherein the apparatus further comprises an activation component to start the measurement of the blood pressure, and wherein the activation component is configured to be held in the hand of the subject along with the second ECG electrode.

8. Apparatus as claimed in claim 6, wherein the apparatus further comprises an activation component to start the measurement of the blood pressure, and wherein the activation component is configured to be held in a hand of the subject, the control unit being configured to respond to the activation of the activation component to obtain the first measurement of the physiological characteristic as skin conductivity/conductance of the subject measured using the skin conductance electrodes.

9. A method of assessing the reliability of a measurement of blood pressure of a subject, comprising:
   obtaining a first measurement of at least one physiological characteristic of the subject that is indicative of the level of pain and/or stress of the subject, wherein the first measurement is made prior to a measurement of blood pressure being made;
   obtaining the measurement of blood pressure of the subject;
   obtaining a second measurement of the at least one physiological characteristic of the subject, wherein the second measurement is made after the measurement of blood pressure is made and prior to a subsequent measurement of blood pressure being made; and
   determining if the measurement of blood pressure is reliable based on the first measurement and the second measurement, wherein the measurement of blood pressure is determined to be reliable if the first measurement of the at least one physiological characteristic and the second measurement of the at least one physiological characteristic indicate a low level of pain and/or stress;
   wherein the measurement of blood pressure is made using an inflatable cuff around a limb of the subject a pump to inflate the cuff, and a pressure sensor to measure air pressure inside the inflatable cuff;
   wherein the inflatable cuff further comprises a physiological characteristic sensor to obtain measurements of the at least one physiological characteristic; and
   wherein the physiological characteristic is heart rate variability or skin conductance/conductivity.

10. A method as claimed in claim 9, wherein an operation of determining if the measurement of blood pressure is reliable comprises:
   determining that the measurement of blood pressure is not reliable if at least one of the first measurement of the at least one physiological characteristic and the second measurement of the at least one physiological characteristic indicate a high level of pain and/or stress.

11. A method as claimed in claim 9, wherein an operation of determining if the measurement of blood pressure is reliable comprises:
   determining that the measurement of blood pressure is not reliable if the first measurement of the at least one physiological characteristic and the second measurement of the at least one physiological characteristic indicate different levels of pain and/or stress.

12. A method as claimed in claim 9, wherein the method further comprises:
repeating the operation of obtaining if the measurement of blood pressure is not determined to be reliable.

13. A method as claimed in claim 9, wherein an operation of obtaining a measurement of blood pressure of the subject is performed if the first measurement of the at least one physiological characteristic indicates a low level of pain and/or stress.

14. A method as claimed in claim 9, wherein, if the first measurement of the at least one physiological characteristic indicates a high level of pain and/or stress, wherein the method further comprises:
obtaining one or more further measurements of the at least one physiological characteristic of the subject, wherein the one or more further measurements are made prior to the measurement of blood pressure being made; and
wherein the operation of obtaining a measurement of blood pressure of the subject is performed once a further measurement is made that indicates a low level of pain and/or stress.

15. A computer program product comprising a computer readable medium, the computer readable medium having computer readable code embodied therein, the computer readable code being configured such that, on execution by a suitable computer or processor, the computer or processor is caused to:

obtain a first measurement of at least one physiological characteristic of the subject that is indicative of the level of pain and/or stress of the subject, wherein the first measurement is made prior to a measurement of blood pressure being made;
obtain the measurement of blood pressure of the subject;
obtain a second measurement of the at least one physiological characteristic of the subject, wherein the second measurement is made after the measurement of blood pressure is made and prior to a subsequent measurement of blood pressure being made; and
determine if the measurement of blood pressure is reliable based on the first measurement and the second measurement, wherein the measurement of blood pressure is determined to be reliable if the first measurement of the at least one physiological characteristic and the second measurement of the at least one physiological characteristic indicate a low level of pain and/or stress;
wherein the measurement of blood pressure is made using an inflatable cuff around a limb of the subject, a pump to inflate the cuff, and a pressure sensor to measure air pressure inside the inflatable cuff;
wherein the inflatable cuff further comprises a physiological characteristic sensor to obtain measurements of the at least one physiological characteristic; and
wherein the physiological characteristic is heart rate variability or skin conductance/conductivity.

* * * * *